United States Patent [19]

Kataoka et al.

[11] 4,153,993
[45] May 15, 1979

[54] BEARING MECHANISM FOR A DENTAL HANDPIECE

[75] Inventors: Kenzo Kataoka; Takahiko Nose, both of Uji, Japan

[73] Assignee: Kabushiki Kaisha Morita Seisakusho, Kyoto, Japan

[21] Appl. No.: 871,213

[22] Filed: Jan. 23, 1978

[30] Foreign Application Priority Data

Jan. 25, 1977 [JP] Japan .................................. 52-7449

[51] Int. Cl.² ................................................ A61C 1/12
[52] U.S. Cl. .................................. 32/27; 32/DIG. 6; 308/10
[58] Field of Search ............. 32/27, DIG. 6; 415/503; 308/10, DIG. 1

[56] References Cited

U.S. PATENT DOCUMENTS

| Re. 25,964 | 2/1966 | Williams et al. | 32/27 |
| 3,175,293 | 3/1965 | Borden | 415/503 |
| 3,365,425 | 12/1967 | Carriere et al. | 308/10 |
| 3,380,162 | 4/1968 | Heathe | 32/27 |
| 3,476,449 | 11/1969 | Chaboseau et al. | 308/10 |

FOREIGN PATENT DOCUMENTS 1018684  2/1966  United Kingdom ..................... 415/503

Primary Examiner—Russell R. Kinsey
Assistant Examiner—John J. Wilson
Attorney, Agent, or Firm—Koda and Androlia

[57] ABSTRACT

A bearing for an air driven turbine operated dental handpiece of the type including a turbine rotor provided in a casing and having blade elements coupled to a shaft member. The bearing includes a first air bearing formed circumferentially about the shaft member, a second air bearing including a small gap formed between the end of the shaft and an inside surface of the casing and a means for introducing compressed air into the small gap and a pair of opposed magnets of the same polarity provided respectively in the end of the shaft member and the inside surface of the casing whereby the axial load on the turbine rotor is resisted not only by the second air bearing but also by the magnetic repulsive force of the magnets.

5 Claims, 4 Drawing Figures

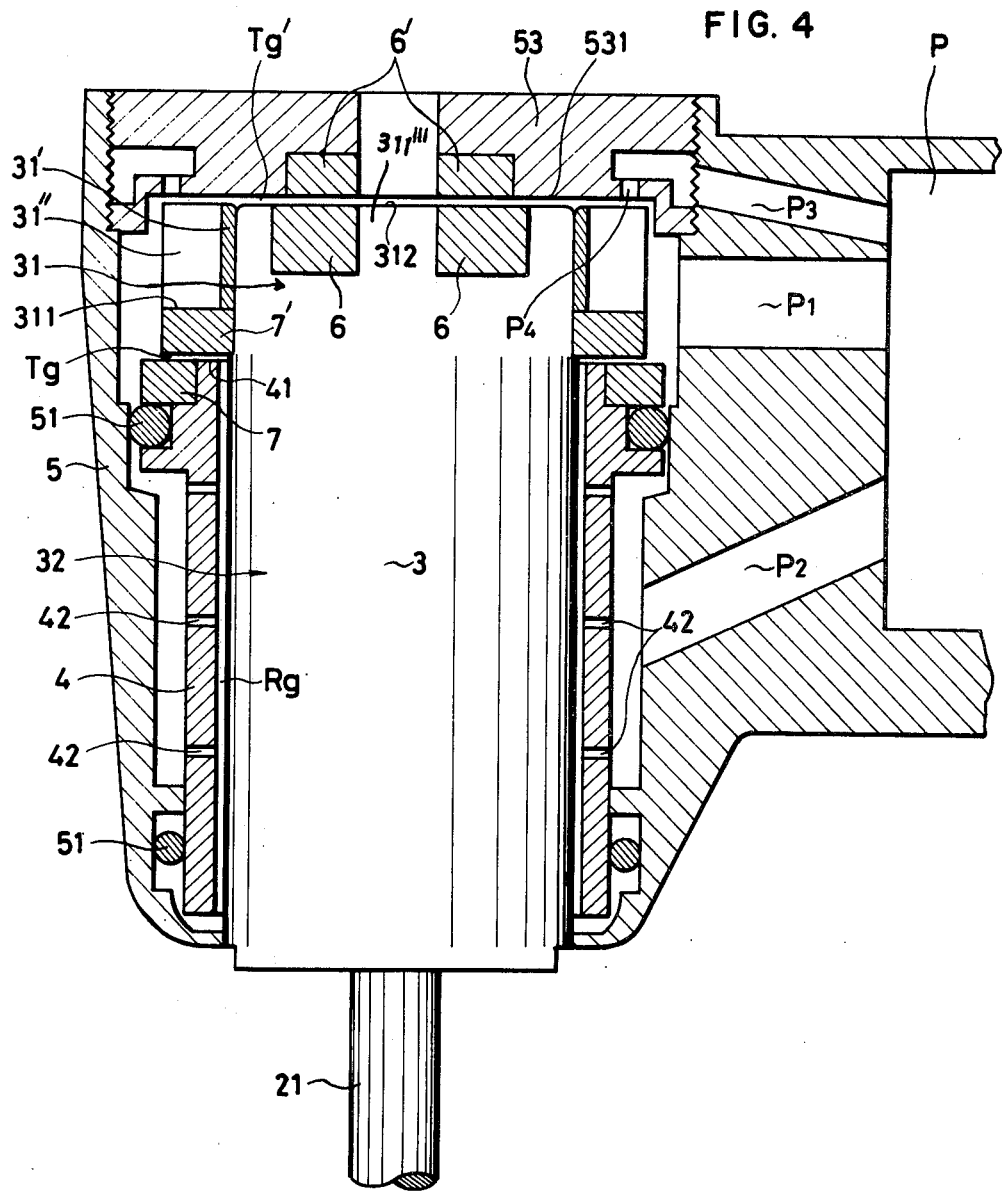

BEARING MECHANISM FOR A DENTAL HANDPIECE

BACKGROUND OF THE INVENTION

1. Field of Invention

This invention relates to air driven turbine handpieces for use in dental treatment and more particularly to air bearings for such air driven turbine handpieces.

2. Prior Art

As is well known, the cutting of teeth is one of the items of dental treatment. As shown in FIG. 1, the cutting of the teeth is carried out by a dental handpiece 1. The handpiece 1 is so constructed that a cutting tool 2 can be attached to the end of the handpiece 1 in such a manner that the tool 2 is turned at a high rate of speed to thereby cut the teeth. In order to reduce the pain for the patient and to increase durability and cutting efficiency of the cutting tool, the tool 2 must be turned at a high speed.

For safety sake, the speed of rotation of the tool 2 must be limited and therefore is limited to approximately 500,000 rpm under no load conditions. In order to meet such a demand, an air bearing journaled handpiece using an air bearing has been developed. The air bearing journaled handpiece offers the advantages that it reduces the pain to the patient and increases cutting efficiency to a greater degree than the prior art ball bearing handpieces.

A conventional prior art air bearing journaled handpiece is shown in FIG. 2. As shown in FIG. 2, the handpiece comprises a turbine rotor 3 having shaft members 32 and 32' provided on both ends of the rotor 3 and extending along the axis of rotation of the rotor 3. Blade elements 31 are integrally provided on the rotor 3 bearings 42 and 42' support the shaft member 32 and 32'. The bearings 42 and 42' are each generally fixedly supported by O-rings 51 and 52 in casing 5.

The bearing mechanism of the type described above has a disadvantage in that the bearings 42 and 42' are axially moved by the twist or dimensional error of the O-rings 51 and 52 which in turn produces non-uniformity in the pressure distribution in the gaps 34 and 34' formed between the shaft member 32 and 32' of the turbine rotor 3 and the bearings 42 and 42' and affect a reduction in the load carrying capacity of the bearings 42 and 42'. Since the axial length of the gaps 34 and 34' is relatively short, the pressure distribution in each of the gaps 34 and 34' becomes parabolic in the axial direction of the gaps 34 and 34'. As a result, the load carrying capacity of the bearing is further reduced and therefore even the smallest load torque reduces the number of rotations of the tool 2.

To overcome these disadvantages, the present applicant filed an application in the Japanese Patent Office on Dec. 28, 1972 which disclosed a turbine engine driven air bearing handpiece for dental treatment designed to overcome these disadvantages. Such Japanese patent was registered on Apr. 28, 1977 and has a Japanese Pat. No. 856133. This handpiece is shown in FIG. 3.

As shown in FIG. 3, the shaft member 32 is in connected to only one side of the blade element 31 and no shaft member is provided on the other side of the blade element 31. Namely, the shaft member 32 is journaled by air bearings in the direction of thrust between a radial gap $R_g$ and thrust gaps $T_g$ and $T_g'$ formed in pairs forwardly and rearwardly of the blade element 31. The radial gap $R_g$ is formed between the bearings 42 provided by O-rings 51 inside the casing that correspond with the shaft member 32. According to the construction described, an ideal number of rotations (more than 400,000 rpm) for tooth cutting can be obtained and furthermore even if there is twist or a dimensional error in the O-rings 51, such twist or error ends in only one side and there is no possibility of the axis of rotation of the shaft member 32 moving during rotation of the shaft member 32. As a result, the bearing mechanism for a dental handpiece capable of reducing the disagreeable feeling and pain for the patient and having excellent rotational characteristics is achieved.

However, as a result of this construction, the air bearing mechanism makes it impossible to enlarge the thrust gaps $T_g$ and $T_g'$ as an area of bearing with respect to the direction of thrust. Accordingly a new problem has been created. In operation when the operator depresses the cutting tool strongly to drill a tooth, the area above the bearings cannot sufficiently resist the axial load in the direction of thrust. Accordingly, the thrust bearing capacity based exclusively on the air pressure inside the gaps $T_g$ and $T_g'$ cannot resist the load and consequently the rear end surface 312 of the blade element 31 is brought by rotation into contact with the inside wall surface of an end cover 53. As a result friction is created and the life of the handpiece 1 and the number of rotations of the turbine rotor 3 is decreased when the tool 2 is put under load. Therefore the cutting tool 2 which is coupled to the turbine rotor 3 and rotates in synchronism thereto receives these adverse effects and turns at a lower rpm.

SUMMARY OF THE INVENTION

Accordingly, it is the general object of the present invention to provide an air bearing for an air driven turbine operated journaled dental handpiece which resists the axial load in the direction of thrust.

It is another object of the present invention to provide a bearing for an air driven turbine operated journaled dental handpiece which allows the tool to turn under no load conditions at a rate of rotation greater than 400,000 rpm.

In keeping with the principles of the present invention, the objects are accomplished by a bearing for an air driven turbine operated journaled dental handpiece of the type including a turbine rotor provided in a casing and having blade elements coupled to a shaft member. The bearing includes a first air bearing formed circumferentially about the shaft member, a second air bearing provided between the top surface of the rotor and the inside surface of the casing, a third air bearing provided between the bottom surface of the rotor and the inside surface of the casing and a pair of opposed magnets of the same polarity provided respectively in the end of the top surface of the rotor and the inside surface of the casing whereby the axial load on the turbine rotor is resisted by not only the second and third air bearings but also by the magnetic repulsive force of the magnets.

BRIEF DESCRIPTION OF THE DRAWINGS

The above mentioned features and objects of the present invention will become more apparent with reference to the following description taken in conjunction with the accompanying drawings, wherein like referenced numerals denote like elements and in which:

FIG. 4 is a longitudinal sectional view of the essential parts of a preferred embodiment in accordance with the teachings of the present invention.

DETAILED DESCRIPTION OF THE INVENTION

Figure 1:
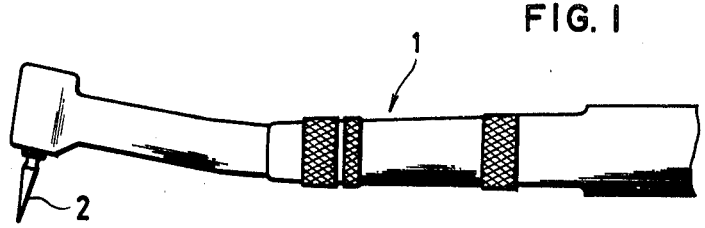
FIG. 1 is a perspective view of a dental handpiece.
Figure 3:
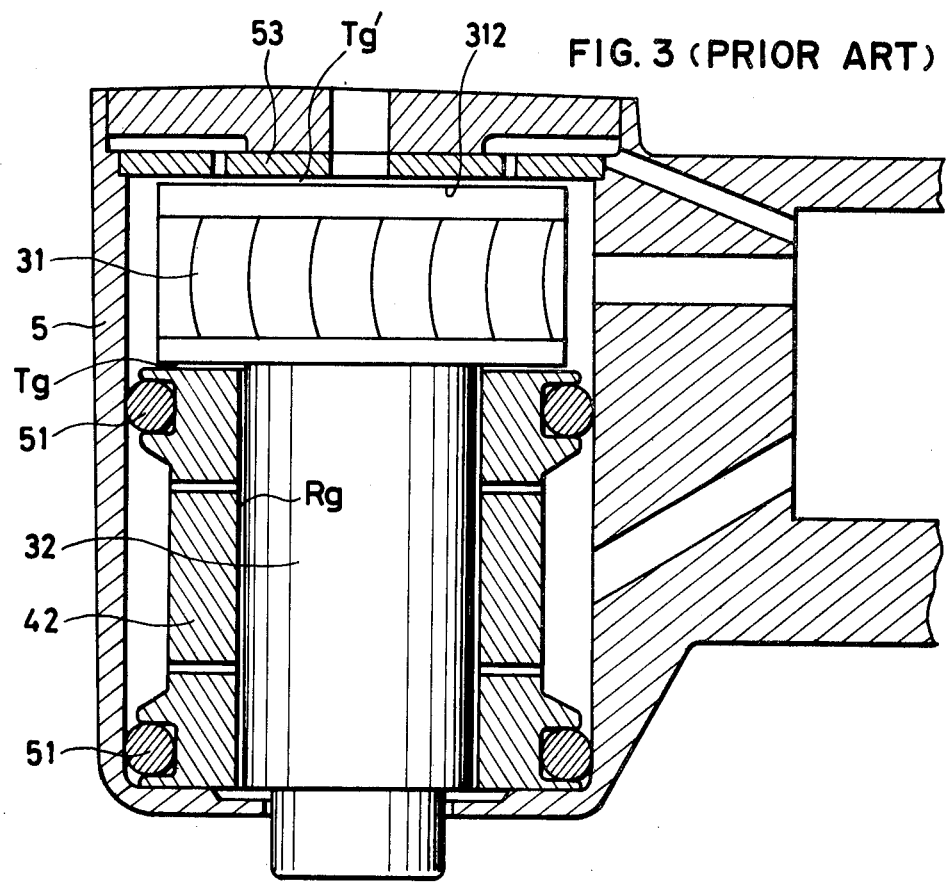
FIG. 3 is a longitudinal sectional view of the essential part of a second prior art air bearing mechanism for dental handpieces.
Figure 2:
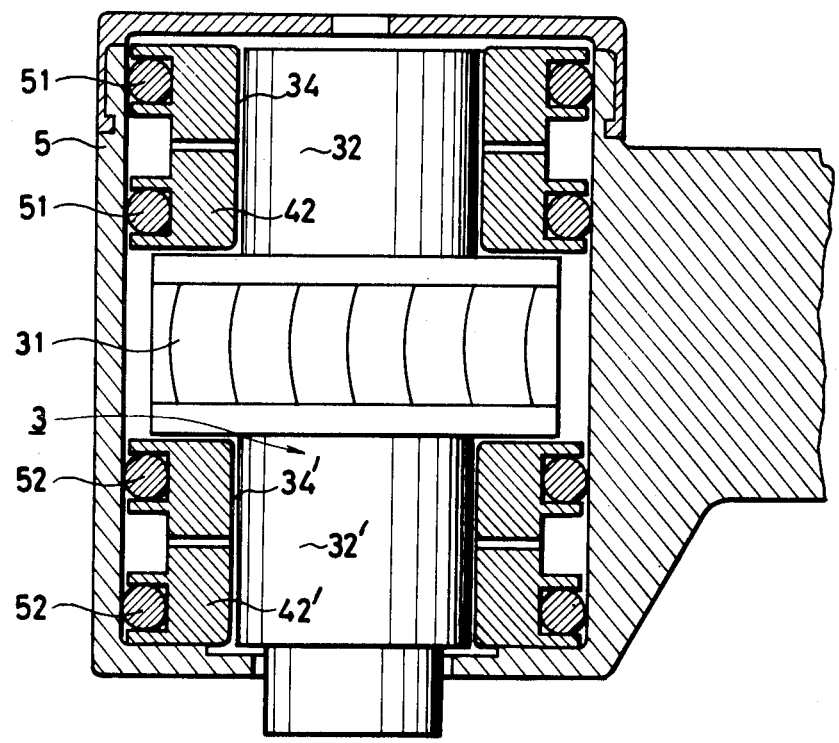
FIG. 2 is a longitudinal sectional view of the essential part of the bearing mechanism of a convention type air bearing dental handpiece.

Referring more particularly to the drawings, shown in FIG. 4 is a preferred embodiment in accordance with the teachings of the present invention. Those elements in FIG. 4 which are the same as in FIG. 2 are given like referenced numerals and a description of their interconnection in operation will be omitted.

In FIG. 4, the preferred embodiment comprises a turbine rotor 3 which includes blade elements 31 coupled to a shaft member 32. Shaft member 32 of turbine rotor 3 is air journaled by bearings 4 which circumferentially surround shaft member 32. A casing 5 encloses the bearings 4 and an inlet 53 is provided in the casing 5. A radial gap Rg is formed between the shaft member 32 of the turbine rotor 3 and the bearings 4. Thrust gaps Tg and Tg' are formed respectively between the top surface of the rotor 3 and the undersurface of the end lid 53 and the bottom surface of the rotor 3 and the end of bearing 4.

A pair of magnets 6 and 6' of the same polarity are provided opposing each other respectively in the top surface of the rotor 3 and the bottom surface of the end lid 53. Opposed pair of magnets 7 and 7' of the same polarity are provided respectively in the rear end face 41 of bearing 4 and the bottom surface 311 of the rotor 3.

Furthermore a tool shaft 21 of cutting tool 2 is clamped firmly by a suitable chuck mechanism (not shown) on the shaft member 32 and is rotated at high speed in synchronism with the rotation of the turbine rotor 3. The turbine rotor 3 is turned by compressed air fed by an air compressor (not shown) through air passageway P1 and is rotated at a high speed (400,000 to 500,000 rpm and no load) by the air acting directly onto the blade element 31. Compressed air is also supplied through passageways P2, P3 and P4.

The blade element 31 comprises a blade shaft 311''' extending to the rear end side of shaft 32 on attachment ring 31' and blades 31'' provided at specific intervals in the radial direction on the outside of ring 31'. The bearing 4 is cylindrical in shape and opens at the front and rear ends and is provided in the axial direction of its wall thickness with a plurality of air holes 42. The bearing 4 is fixed to the intercircumferential wall of the casing 5 by elastic O-rings 51. The radial gap Rg is formed between the bearing 4 and a shaft member 32 of the turbine rotor 3. The front side thrust gap Tg of thrust gaps Tg and Tg' is formed between the magnet means 7 secured to the front end face 311 of the blade element 31 and the rear end face 41 of the bearing 4 and the magnet means 7 secured to the rear end face 41. The backside thrust gap Tg' is also formed between the front end face 531 of the lid 53 and the rear end face 312 of the blade element 31. Compressed air from the air supply passageway P is supplied through branch passageway P2 and air holes 42 into the radial gap Rg. Compressed air is supplied to thrust gaps Tg and Tg' so as to journal the turbine rotor 5 in interbearings with respect to the thrust and radial directions by compressed air fed through passageway P1, P3 and P4. The magnet means 6 and 6' and 7 and 7' are ring shaped permanent magnets respectively disposed in opposed relation to each other. Magnets 6 and 6' are provided flush in the front end face 531 of end lid 53 and rear end face 312 of blade element 31. Magnets 7 and 7' are also provided respectively flush with the rear end face 41 of bearing 4 and the front end face 311 of blade element 31.

In operation, when an operator drills a tooth of a patient by strongly pressing the cutting tool 2 of the handpiece 1 against the tooth, the turbine rotor 3 is heavily subjected to a load in the axial direction of thrust. Since the magnet means 6 and 6' and 7 and 7' are oriented to be in the same polarity, the repulsive forces can resist the axial load of the turbine rotor 3 in the direction of thrust. In other words, because of the repulsive force of the magnet increases in inverse proportion to the square of the distance, the repulsive force between the magnets increases dramatically when the thrust gap Tg' is decreased as a result of the thrust load. As a result there is little or no possibility of the front end face 531 of the end lid 53 and the rear end 312 of the blade element 31 from contacting each other. Accordingly, the turning torque of the turbine rotor 3 and the cutting tool 2 which rotates in synchronism therewith is free from adverse effects and the rate of rotation of the cutting tool 2 is not reduced and the patient does not receive undue stimulation and pain.

Also, when the turbine rotor 3 is journaled in the air bearings, the normal rotation of rotor 3 is achieved by the balance of air pressure in the pair of front and rear thrust gaps Tg and Tg' and the balance in the repulsive forces of the magnet means 6 and 6' and 7 and 7'.

It should be apparent to one skilled in the art that the above described embodiments are merely illustrative of but one of the many possible specific embodiments which represent the application of the principles of the present invention. Numerous and varied other arrangements can be readily devised by those skilled in the art without departing from the spirit and scope of the invention.

We claim:

1. A bearing mechanism for an air driven turbine operated dental handpiece of the type including a turbine rotor provided in a casing and having blade elements coupled to a shaft member, said bearing comprising:

a first air bearing formed circumferentially about said shaft member;

a second air bearing provided between the top of said rotor and an inside surface of said casing; and a pair of opposed magnets of the same polarity provided respectively in the top surface of said rotor and the inside surface of said casing whereby axial thrust load on said turbine rotor is resisted by not only said second air bearing but also by the magnetic repulsive force of said pair of magnets.

2. A bearing according to claim 1 further comprising a third air bearing provided between a bottom surface of said rotor and an end of said first air bearing.

3. A bearing according to claim 2 further comprising a pair of opposed magnets of the same polarity provided respectively on a bottom surface of said rotor and said end of said first air bearing.

4. A bearing for an air driven turbine operated dental handpiece of the type including a turbine rotor provided in a casing and having blade elements coupled to a shaft member, said bearing comprising:

a first air bearing formed circumfentially about said shaft member;

a second air bearing provided between the top surface of said rotor and an inside surface of said casing, said second air bearing comprising a gap between said top surface of said rotor and said inside surface of said casing into which compressed air is introduced;

a third air bearing provided between a bottom surface of said rotor and an end of said first air bearing, said third air bearing comprising a gap between said bottom surface of said rotor and an end of said first air bearing into which compressed air is introduced;

a first pair of opposed magnets of the same polarity provided respectively in said top surface of said rotor and said inside surface of said casing; and a second pair of opposed magnets of the same polarity provided respectively in said bottom surface of said rotor and said end of said first air bearing whereby axial thrust loads applied to said air driven turbine are resisted by not only said second and third air bearings but also the magnetic repulsive force of said first and second pair of magnets.

5. A bearing according to claim 4 wherein said first and second pairs of opposed magnets each are formed in a ring like shape.

* * * * *